US012636491B2

(12) United States Patent
Carter

(10) Patent No.: US 12,636,491 B2
(45) Date of Patent: May 26, 2026

(54) ELECTROPORATION SHIELD FOR IMPLANTABLE ELECTRODES

(71) Applicant: Cochlear Limited, Macquarie University (AU)

(72) Inventor: Paul Michael Carter, Galson (AU)

(73) Assignee: Cochlear Limited, Macquarie University (AU)

( * ) Notice: Subject to any disclaimer, the term of this patent is extended or adjusted under 35 U.S.C. 154(b) by 637 days.

(21) Appl. No.: 18/041,657

(22) PCT Filed: Aug. 18, 2021

(86) PCT No.: PCT/IB2021/057593
§ 371 (c)(1),
(2) Date: Feb. 14, 2023

(87) PCT Pub. No.: WO2022/038535
PCT Pub. Date: Feb. 24, 2022

(65) Prior Publication Data
US 2023/0302275 A1     Sep. 28, 2023

Related U.S. Application Data

(60) Provisional application No. 63/067,920, filed on Aug. 20, 2020.

(51) Int. Cl.
*A61N 1/08* (2006.01)
*A61N 1/32* (2006.01)
*A61N 1/40* (2006.01)

(52) U.S. Cl.
CPC .............. *A61N 1/08* (2013.01); *A61N 1/327* (2013.01); *A61N 1/40* (2013.01)

(58) Field of Classification Search
CPC . A61N 1/08; A61N 1/327; A61N 1/40; A61N 1/0541; A61N 1/36038; A61N 1/3756
See application file for complete search history.

(56) References Cited

U.S. PATENT DOCUMENTS 6,641,564 B1 * 11/2003 Kraus ................. A61M 25/065
604/110
9,533,138 B2     1/2017 Housley
(Continued)

FOREIGN PATENT DOCUMENTS

EP     3010582 A1    4/2016
EP     3313505 A1    5/2018
(Continued)

OTHER PUBLICATIONS

International Search Report and Written Opinion in counterpart International Application No. PCT/IB2021/057593, mailed Nov. 23, 2021, 11 pages.
(Continued)

*Primary Examiner* — Mark W. Bockelman
(74) *Attorney, Agent, or Firm* — Edell, Shapiro & Finnan, LLC

(57) ABSTRACT

Presented herein is an electroporation shield configured to be removably coupled to an implantable stimulating assembly that includes one or more stimulation electrodes. The electroporation shield is coupled to stimulating assembly such that the electroporation shield electrically insulates the one or more of the stimulation electrodes from an electroporation electrical field generated by one or more electroporation electrodes coupled to the electroporation shield. The electroporation shield may be coupled to the stimulating assembly in a manner that facilitates removal of the electroporation shield and the one or more electroporation electrodes. After electroporation, without having to remove or reinsert the stimulating assembly, thereby exposing the one or more stimulation electrodes to the cells of the recipient for subsequent delivery of stimulation.

20 Claims, 12 Drawing Sheets

(56)                    References Cited

U.S. PATENT DOCUMENTS

| | | | |
|---|---|---|---|
| 11,013,917 | B2 | 5/2021 | Housley |
| 11,376,423 | B2 | 7/2022 | Lehmann et al. |
| 2009/0254019 | A1* | 10/2009 | Gehl .................. A61B 18/1477 |
| | | | 604/21 |
| 2010/0298761 | A1* | 11/2010 | Staal ...................... A61N 1/327 |
| | | | 604/20 |
| 2012/0191032 | A1 | 7/2012 | Housley |
| 2015/0306416 | A2 | 10/2015 | Kumar et al. |
| 2016/0129246 | A1 | 5/2016 | Housley et al. |
| 2017/0173323 | A1 | 6/2017 | Housley |
| 2017/0368331 | A1 | 12/2017 | Murphy et al. |
| 2018/0169399 | A1 | 6/2018 | Housley et al. |
| 2019/0133671 | A1 | 5/2019 | Davalos et al. |
| 2019/0351220 | A1 | 11/2019 | Lehmann et al. |
| 2022/0032045 | A1 | 2/2022 | Murphy et al. |

FOREIGN PATENT DOCUMENTS

| | | | |
|---|---|---|---|
| EP | 3893986 | A1 | 10/2021 |
| WO | 2019-213421 | A1 | 11/2019 |
| WO | 2021072507 | A1 | 4/2021 |
| WO | 2022/018532 | A1 | 1/2022 |
| WO | 2022/038535 | A1 | 2/2022 |
| WO | 2022/058830 | A1 | 3/2022 |
| WO | 2022/106928 | A1 | 5/2022 |

OTHER PUBLICATIONS

Pinyon, J. L. et al. 'Close-field electroporation gene delivery using the cochlear implant electrode array enhances the bionic ear', Science translational medicine, 2014, vol. 6, No. 233, p. 233ra54, internal pp. 1-10.

Extended European Search Report in counterpart European Application No. 21857880.5-1122, mailed Jul. 22, 2024, 7 pages.

* cited by examiner

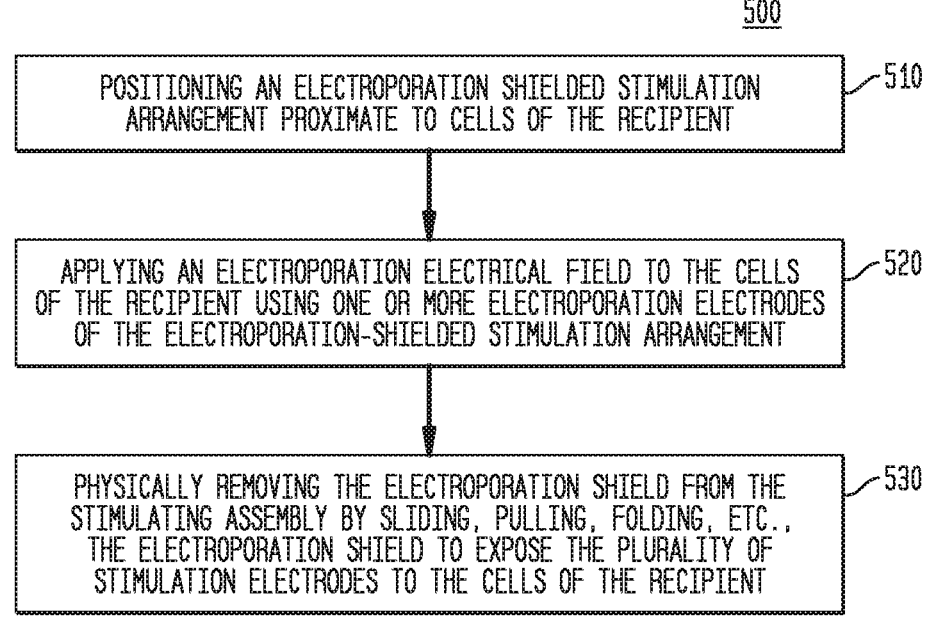

500

POSITIONING AN ELECTROPORATION SHIELDED STIMULATION
ARRANGEMENT PROXIMATE TO CELLS OF THE RECIPIENT ⟋510

APPLYING AN ELECTROPORATION ELECTRICAL FIELD TO THE CELLS
OF THE RECIPIENT USING ONE OR MORE ELECTROPORATION ELECTRODES
OF THE ELECTROPORATION-SHIELDED STIMULATION ARRANGEMENT ⟋520

PHYSICALLY REMOVING THE ELECTROPORATION SHIELD FROM THE
STIMULATING ASSEMBLY BY SLIDING, PULLING, FOLDING, ETC.,
THE ELECTROPORATION SHIELD TO EXPOSE THE PLURALITY OF
STIMULATION ELECTRODES TO THE CELLS OF THE RECIPIENT ⟋530

FIG. 8

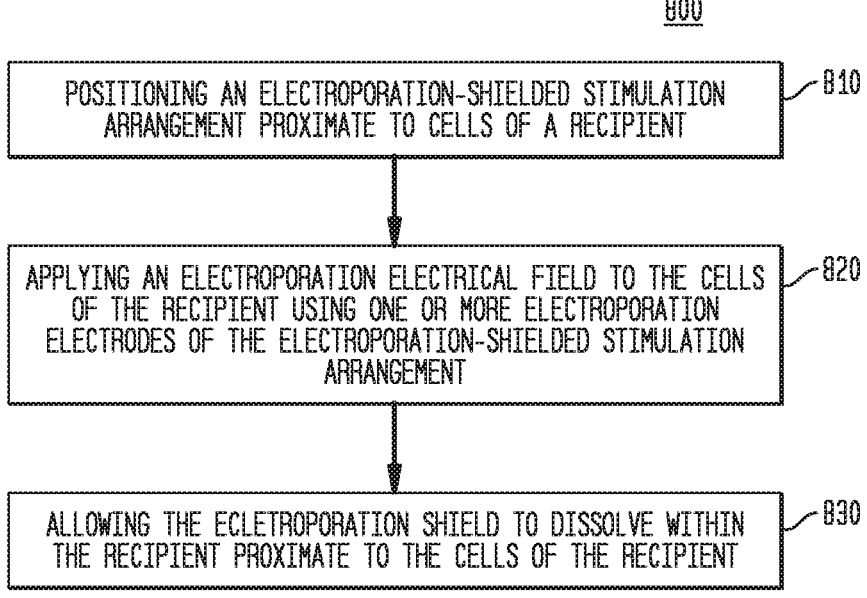

800

POSITIONING AN ELECTROPORATION-SHIELDED STIMULATION ARRANGEMENT PROXIMATE TO CELLS OF A RECIPIENT — 810

APPLYING AN ELECTROPORATION ELECTRICAL FIELD TO THE CELLS OF THE RECIPIENT USING ONE OR MORE ELECTROPORATION ELECTRODES OF THE ELECTROPORATION-SHIELDED STIMULATION ARRANGEMENT — 820

ALLOWING THE ECLETROPORATION SHIELD TO DISSOLVE WITHIN THE RECIPIENT PROXIMATE TO THE CELLS OF THE RECIPIENT — 830

FIG. 9
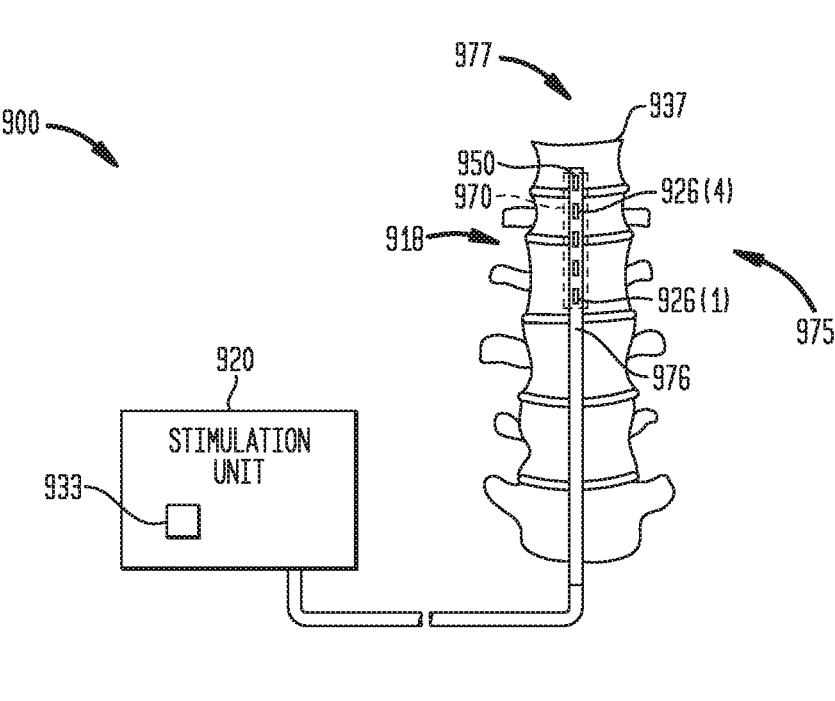

FIG. 10

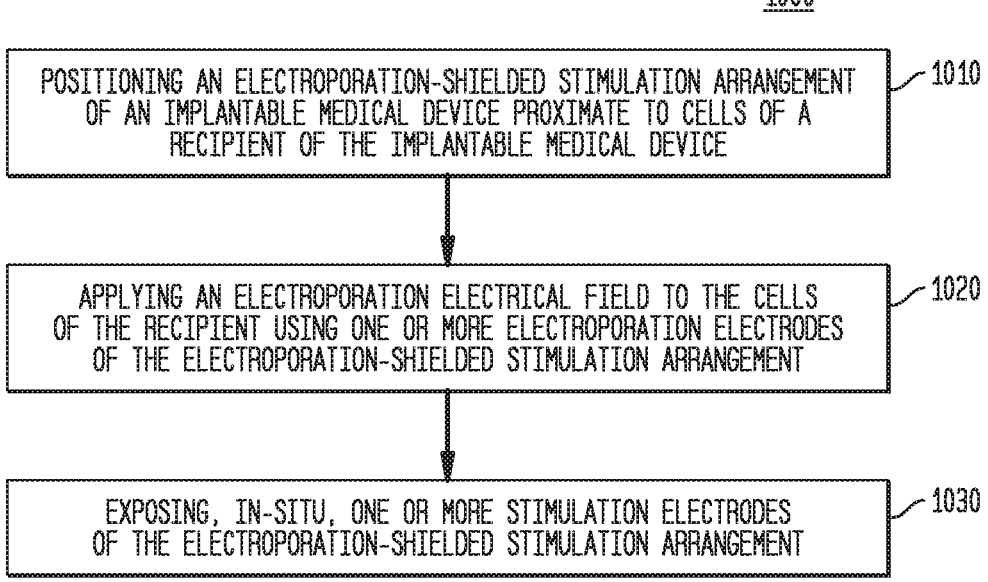

1000

POSITIONING AN ELECTROPORATION-SHIELDED STIMULATION ARRANGEMENT OF AN IMPLANTABLE MEDICAL DEVICE PROXIMATE TO CELLS OF A RECIPIENT OF THE IMPLANTABLE MEDICAL DEVICE — 1010

APPLYING AN ELECTROPORATION ELECTRICAL FIELD TO THE CELLS OF THE RECIPIENT USING ONE OR MORE ELECTROPORATION ELECTRODES OF THE ELECTROPORATION-SHIELDED STIMULATION ARRANGEMENT — 1020

EXPOSING, IN-SITU, ONE OR MORE STIMULATION ELECTRODES OF THE ELECTROPORATION-SHIELDED STIMULATION ARRANGEMENT — 1030

FIG. 11

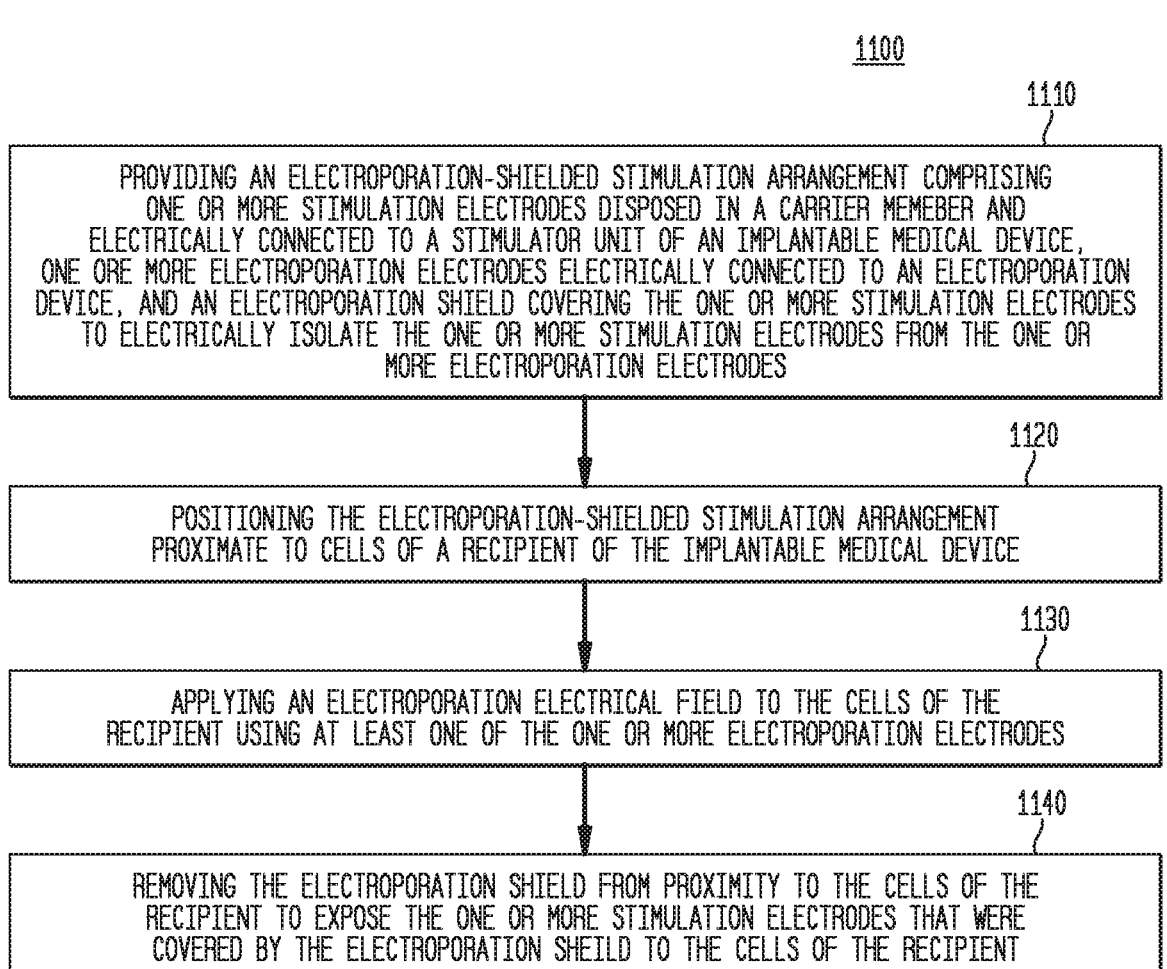

1100

1110

PROVIDING AN ELECTROPORATION-SHIELDED STIMULATION ARRANGEMENT COMPRISING
ONE OR MORE STIMULATION ELECTRODES DISPOSED IN A CARRIER MEMEBER AND
ELECTRICALLY CONNECTED TO A STIMULATOR UNIT OF AN IMPLANTABLE MEDICAL DEVICE,
ONE ORE MORE ELECTROPORATION ELECTRODES ELECTRICALLY CONNECTED TO AN ELECTROPORATION
DEVICE, AND AN ELECTROPORATION SHIELD COVERING THE ONE OR MORE STIMULATION ELECTRODES
TO ELECTRICALLY ISOLATE THE ONE OR MORE STIMULATION ELECTRODES FROM THE ONE OR
MORE ELECTROPORATION ELECTRODES

1120

POSITIONING THE ELECTROPORATION-SHIELDED STIMULATION ARRANGEMENT
PROXIMATE TO CELLS OF A RECIPIENT OF THE IMPLANTABLE MEDICAL DEVICE

1130

APPLYING AN ELECTROPORATION ELECTRICAL FIELD TO THE CELLS OF THE
RECIPIENT USING AT LEAST ONE OF THE ONE OR MORE ELECTROPORATION ELECTRODES

1140

REMOVING THE ELECTROPORATION SHIELD FROM PROXIMITY TO THE CELLS OF THE
RECIPIENT TO EXPOSE THE ONE OR MORE STIMULATION ELECTRODES THAT WERE
COVERED BY THE ELECTROPORATION SHEILD TO THE CELLS OF THE RECIPIENT

ELECTROPORATION SHIELD FOR IMPLANTABLE ELECTRODES

BACKGROUND

Field of the Invention

The present invention relates generally to electroporation with implantable medical devices, and, more specifically, to electroporation shields for electrodes of implantable medical devices.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect, a method is provided. The method comprises: positioning an electroporation-shielded stimulation arrangement of an implantable medical device proximate to cells of a recipient of the implantable medical device; applying an electroporation electrical field to the cells of the recipient using one or more electroporation electrodes of the electroporation-shielded stimulation arrangement; and exposing, in-situ, one or more stimulation electrodes of the electroporation-shielded stimulation arrangement.

In another aspect, a method is provided. The method comprises: providing an electroporation-shielded stimulation arrangement comprising one or more stimulation electrodes disposed in a carrier member and electrically connected to a stimulator unit of an implantable medical device, one or more electroporation electrodes electrically connected to an electroporation device, and an electroporation shield covering the one or more stimulation electrodes to electrically isolate the one or more stimulation electrodes from the one or more electroporation electrodes; positioning the electroporation-shielded stimulation arrangement proximate to cells of a recipient of the implantable medical device; applying an electroporation electrical field to the cells of the recipient using at least one of the one or more electroporation electrodes; and removing the electroporation shield from proximity to the cells of the recipient to expose the one or more stimulation that were covered by the electroporation shield to the cells of the recipient.

In another aspect, an apparatus is provided. The apparatus comprises: a stimulating assembly of an implantable medical device comprising one or more stimulation electrodes disposed in a carrier member, wherein the stimulating assembly is configured for implantation into a spatial region in a body of a recipient of the implantable medical device; an electroporation shield disposed over the plurality of stimulation electrodes, wherein the electroporation shield has an inner surface abutting the stimulating assembly and the plurality of stimulation electrodes, and an opposite outer surface; and one or more electroporation electrodes coupled to the outer surface of the electroporation shield.

In yet another aspect, an apparatus is provided. The apparatus comprises: a tissue-stimulating prosthesis comprising a stimulating assembly and a plurality of stimulation electrodes disposed on the stimulating assembly, the stimulating assembly being configured to be positioned in a recipient of the tissue-stimulating prosthesis proximate to cells of the recipient; and an electroporation shield removably coupled to the stimulating assembly and disposed over at least one of the plurality of stimulation electrodes of the stimulating assembly, wherein the electroporation shield is configured to electrically insulate the at least one of the plurality of stimulation electrodes from voltages equal to and greater than approximately 100 volts.

In another aspect, an apparatus is provided. The apparatus comprises: a tissue-stimulating prosthesis comprising a stimulating assembly and a plurality of stimulation electrodes disposed on the stimulating assembly, the stimulating assembly being configured to be positioned in a recipient of the tissue-stimulating prosthesis proximate to cells of the recipient; and an electroporation shield removably coupled to the stimulating assembly and disposed over at least one of the plurality of stimulation electrodes of the stimulating assembly, wherein the electroporation shield has a thickness of approximately 5 $\mu$m to approximately 100 $\mu$m, is constructed from silicone or polyurethane, is configured to electrically insulate the at least one of the plurality of stimulation electrodes from voltages equal to and greater than approximately 100 volts, and wherein the electroporation shield has a proximal end and a distal end, and at least one pull tab disposed proximate to the proximal end configured to facilitate removal of the electroporation shield by pulling the electroporation shield along the stimulating assembly of the tissue-stimulating prosthesis and out of proximity to the cells of the recipient.

BRIEF DESCRIPTION OF THE DRAWINGS

Embodiments of the present invention are described herein in conjunction with the accompanying drawings, in which:

FIG. 4A is a schematic diagram of the chemical structure of a portion of the stimulating assembly illustrated in FIG. 3A, in accordance with certain embodiments presented herein;

FIG. 4B is a schematic diagram of the chemical structure of a portion of the stimulating assembly illustrated in FIG. 3A, in accordance with certain embodiments presented herein;

FIG. 5 is a flowchart of a method, in accordance with certain embodiments presented herein;

FIG. 8 is a flowchart of a method, in accordance with certain embodiments presented herein;

FIG. 9 is a schematic diagram of a spinal cord stimulator, in accordance with certain embodiments presented herein;

FIG. 10 is a flowchart of a method, in accordance with certain embodiments presented herein; and FIG. 11 is a flowchart of a method, in accordance with certain embodiments presented herein.

DETAILED DESCRIPTION

Figure 1A:
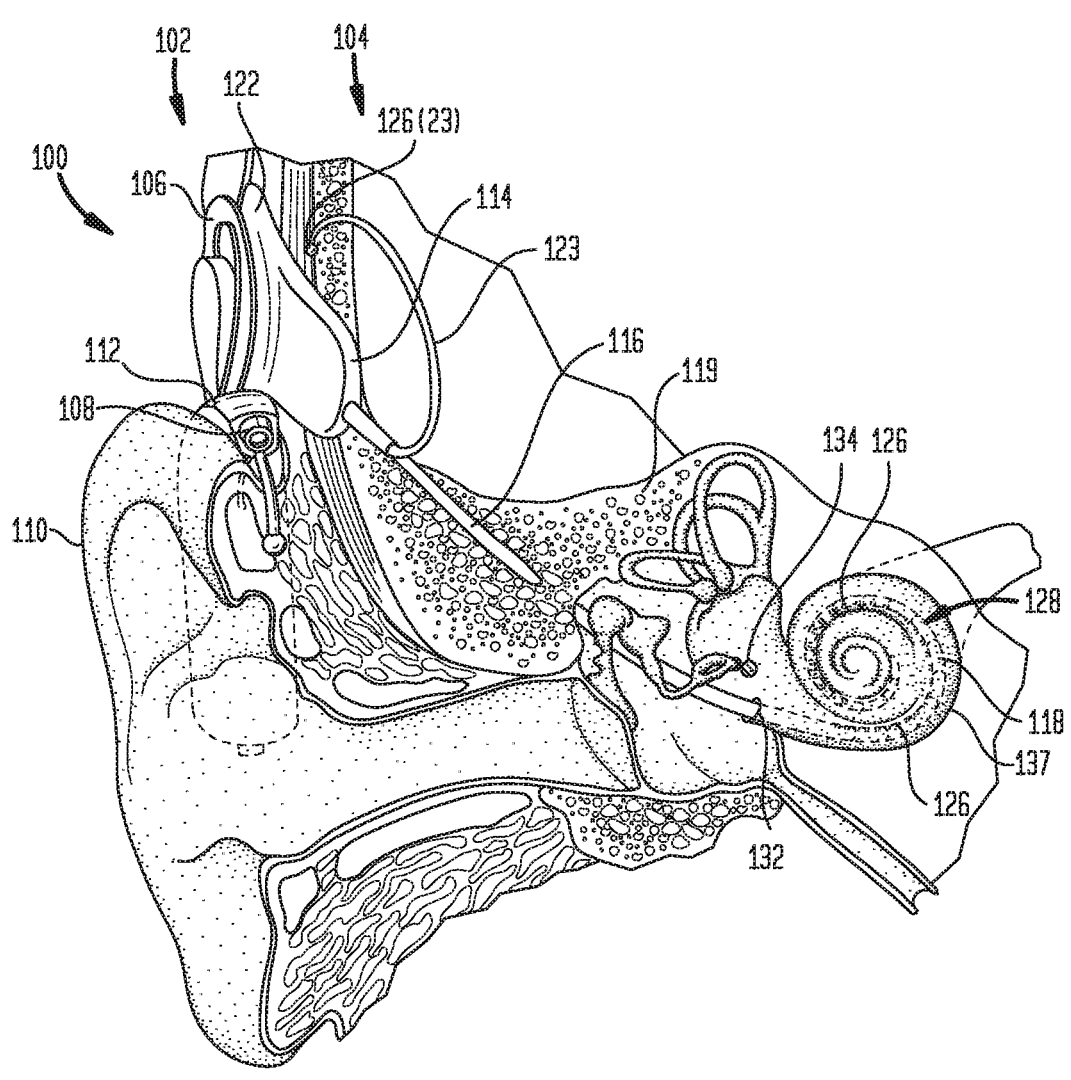
FIG. 1A is a schematic diagram illustrating a cochlear implant, in accordance with certain embodiments presented herein.

Electroporation refers to the application of an electrical field to a cell (e.g., a mesenchymal stem cell) in a manner that creates an electrical potential (i.e., voltage difference) across the cell that, in turn, opens up pores in the membrane of the cell. The electrically opened pores may be used to, for example, allow a treatment substance to enter the cell through the cell membrane (i.e., as the potential difference is applied to the cell, the electrically opened pores in the cell membrane allow material to flow into the cell). After the electrical potential is removed, the pores in the cell membrane close such that the treatment substance remains in the cell. As such, electroporation may be useful with medical devices by altering the biological composition of the cells in a manner that enhances, enables, etc. operation of the medical device.

Successful electroporation requires a cell to be exposed to a large electrical field for a sufficient amount of time so that a desired treatment substance is able to migrate through the cell membrane. Such an electric field, sometimes referred to herein as an "electroporation electrical field," utilizes a high voltage in the range of, for example, approximately 100 Volts (V) to approximately 150 V, over the distance between two or more implanted electrodes positioned in proximity to the target cells (i.e., the cells that are to be electroporated). Such a voltage range is considered "high" because such voltages exceed the typical operating range for electrical components of conventional implantable medical devices. That is, conventional implantable medical devices typically cannot be exposed to such voltages (without incurring damage) and, as a result, electroporation is generally performed using separate devices prior to implantation of an implantable medical device into a recipient.

Presented herein are techniques that enable electroporation of the cells of a recipient of an implantable medical device comprising electrode contacts (electrodes), referred to herein as "a tissue-stimulating prosthesis," while the tissue-stimulating prosthesis is implanted in the recipient. More specifically, tissue-stimulating prostheses in accordance with embodiments presented herein are configured/arranged such that the stimulation electronics (e.g., current sources and integrated circuit) of the prosthesis are insulated from the high voltages used in electroporation. In certain embodiments, an "electrical electroporation shield" or "electroporation shield" is disposed between the stimulation electronics and the implanted electroporation electrodes while the electroporation electrodes generate an electroporation electrical field. The electroporation shield is configured to protect the stimulation electronics from damage (e.g., from the high voltages) during the electroporation.

As noted, there are several types of tissue-stimulating prostheses that deliver stimulation signals (current signals) to compensate for a deficiency in a recipient. Merely for ease of illustration, the embodiments presented herein are primarily described herein with reference to one type of tissue-stimulating prosthesis, namely a cochlear implant. However, it is to be appreciated that the techniques presented herein may be used with other tissue-stimulating prostheses and/or other implantable medical devices, including, for example, other auditory prostheses such as middle ear auditory prostheses (middle ear implants), bone conduction devices, direct acoustic stimulators, electro-acoustic prostheses, auditory brain stimulators, etc. The techniques presented herein may also be used with systems that comprise or include, for example, tinnitus therapy devices, vestibular devices (e.g., vestibular implants), sensors, drug delivery systems, defibrillators, implantable pacemakers, functional electrical stimulation devices, catheters, seizure devices (e.g., devices for monitoring and/or treating epileptic events), sleep apnea devices, spinal cord stimulators, deep brain stimulators, motor cortex stimulators, sacral nerve stimulators, pudendal nerve stimulators, vagus/vagal nerve stimulators, trigeminal nerve stimulators, retinal or other visual prosthesis/stimulators, occipital cortex implants, diaphragm (phrenic) pacers, pain relief stimulators, other neural or neuromuscular stimulators, etc.

Figure 1B:
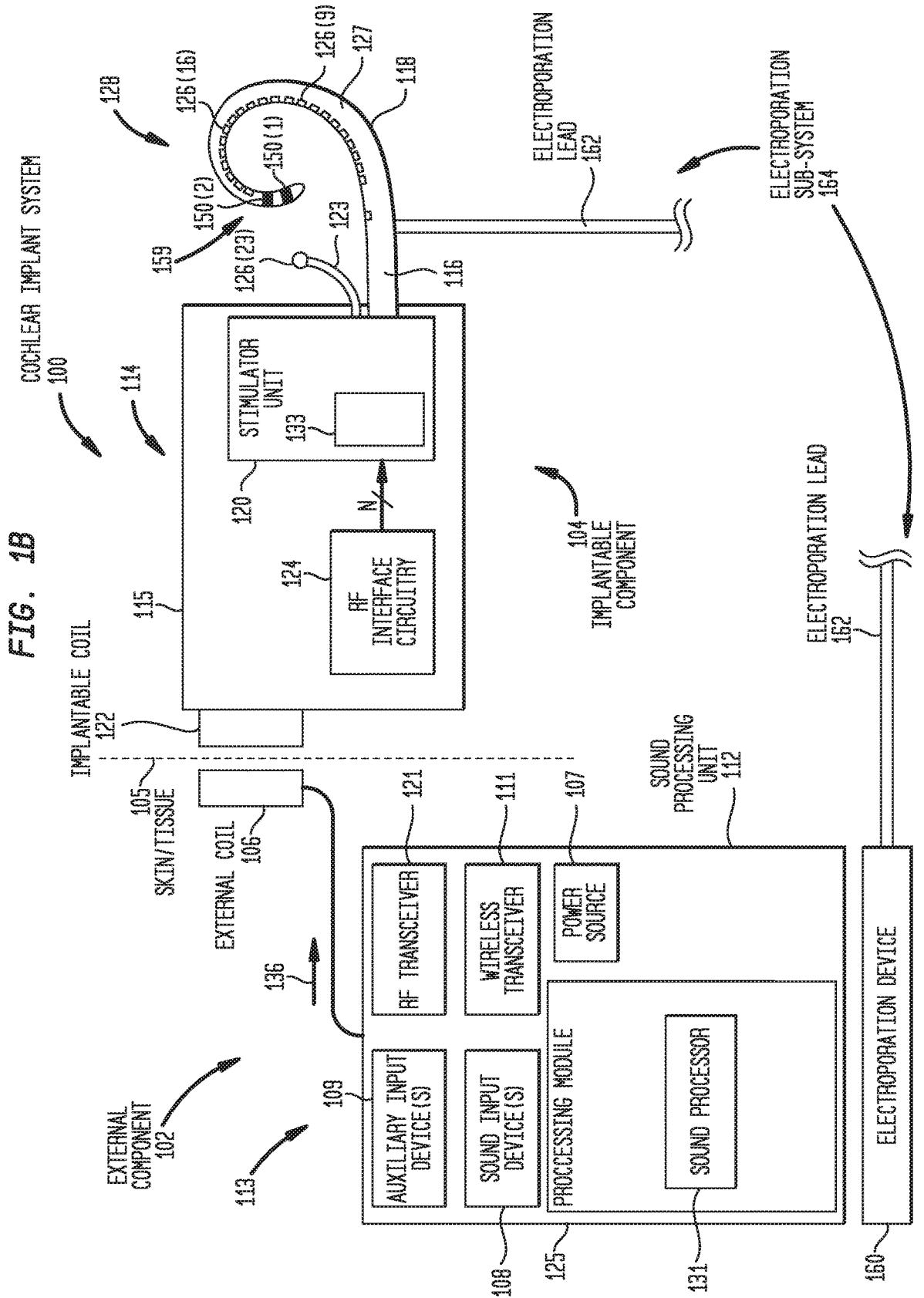
FIG. 1B is a block diagram of the cochlear implant of FIG. 1A.

FIG. 1A is a schematic diagram of an exemplary cochlear implant system 100 configured to implement aspects of the techniques presented herein, while FIG. 1B is a block diagram of the cochlear implant system 100. For ease of illustration, FIGS. 1A and 1B will be described together.

The cochlear implant system 100 comprises an external component 102 and an internal/implantable component 104, which is sometimes referred to herein as "cochlear implant" 104. The external component 102 is directly or indirectly attached to the body of the recipient and typically comprises an external coil 106 and, generally, a magnet (not shown in FIGS. 1A and 1B) fixed relative to the external coil 106. The external component 102 also comprises one or more input elements/devices 113 for receiving input signals at a sound processing unit 112. In this example, the one or more input devices 113 include sound input devices 108 (e.g., microphones positioned by auricle 110 of the recipient, telecoils, etc.) configured to capture/receive input signals, one or more auxiliary input devices 109 (e.g., audio ports, such as a Direct Audio Input (DAI), data ports, such as a Universal Serial Bus (USB) port, cable port, etc.), and a wireless transmitter/receiver (transceiver) 111, each located in, on, or near the sound processing unit 112.

The sound processing unit 112 also includes, for example, at least one battery 107, a radio-frequency (RF) transceiver 121, and a processing module 125. The processing module 125 may comprise a number of elements, including a sound processor 131.

In the examples of FIGS. 1A and 1B, the sound processing unit 112 is a behind-the-ear (BTE) sound processing unit configured to be attached to, and worn adjacent to, the recipient's ear. However, it is to be appreciated that embodiments of the present invention may be implemented by sound processing units having other arrangements, such as by an off-the-ear (OTE) sound processing unit (i.e., a component having a generally cylindrical shape and which is configured to be magnetically coupled to the recipient's head, etc.), a mini or micro-BTE unit, an in-the-canal unit that is configured to be located in the recipient's ear canal, a body-worn sound processing unit, etc.

Returning to the example embodiment of FIGS. 1A and 1B, the implantable component (cochlear implant) 104 comprises an implant body (main module) 114, a lead region 116, and an intra-cochlear stimulating assembly 118, all configured to be implanted under the skin/tissue (tissue) 105 of the recipient. The implant body 114 generally comprises a hermetically-sealed housing 115 in which RF interface circuitry 124 and a stimulator unit 120 are disposed. As described further below, the stimulator unit 120 comprises stimulation electronics 133. The stimulation electronics 133 comprises, among other elements, one or more current sources on an integrated circuit (IC). The implant body 114 also includes an internal/implantable coil 122 that is generally external to the housing 115, but which is connected to the RF interface circuitry 124 via a hermetic feedthrough (not shown in FIG. 1B).

As noted, stimulating assembly 118 is configured to be at least partially implanted in the recipient's cochlea 137. Stimulating assembly 118 includes a carrier member 127 and a plurality of longitudinally spaced intra-cochlear electrodes 126 disposed in/on the carrier member 127. The intra-cochlear electrodes 126 collectively form a contact or electrode array 128 configured to deliver electrical stimulation signals (current signals) to the recipient's cochlea and/or to sink stimulation signals from the recipient's cochlea. FIG. 1A illustrates a specific arrangement in which stimulating assembly 118 comprises twenty-two (22) intra-cochlear electrodes 126, labeled as electrodes 126(1) through 126(22). It is to be appreciated that embodiments presented herein may be implemented in alternative arrangements having different numbers of intra-cochlear electrodes.

Stimulating assembly 118 extends through an opening in the recipient's cochlea (e.g., cochleostomy, the round window, etc.) and has a proximal end connected to stimulator unit 120 via lead region 116 and a hermetic feedthrough (not shown in FIG. 1B). Lead region 116 includes a plurality of conductors (wires) that electrically connect the electrodes 126 to the stimulator unit 120.

Also shown in FIG. 1A is an extra-cochlear electrode 126(23). The extra-cochlear electrode 126(23) is an electrode contact that is configured to, for example, deliver electrical stimulation to the recipient's cochlea and/or to sink current from the recipient's cochlea. The extra-cochlear electrode 126(23) is connected to a reference lead 123 that includes one or more conductors that electrically couple the extra-cochlear electrode 126(23) to the stimulator unit 120.

As noted, the intra-cochlear electrodes 126(1)-126(22) and the extra-cochlear electrode 126(23) can be used post-operatively to stimulate the cochlea 137 of the recipient (i.e., operate as delivery or return paths for current signals to the cochlea 137) that evoke a hearing perception. As such, for ease of description, the intra-cochlear electrodes 126(1)-126 (22) and the extra-cochlear electrode 126(23) are sometimes collectively and generally referred to herein as "stimulation electrodes."

FIGS. 1A and 1B also illustrate that the stimulating assembly 118 includes two (2) electroporation electrode contacts (electrodes) 150(1) and 150(2). As described further below, the electroporation electrodes 150(1) and 150(2) are electrically connected to an external electroporation system/device 160 (shown in FIG. 1B) via an electroporation lead 162 (e.g., one or more wires). As described elsewhere herein, the electroporation electrodes 150(1) and 150(2) can be used to electroporate the recipient's cochlea nerve cells during implantation of the stimulating assembly 118 into the cochlea 137. That is, the electroporation electrodes 150(1) and 150(2) may be configured to source, sink, or both source and sink electroporation signals (generated by external electroporation device 160) that result in the application of an electroporation electrical field to the nerve cells of the cochlea 137. Thereafter, the electroporation electrodes 150(1) and 150(2) can be electrically isolated from the external electroporation device 160 (e.g., electrically disconnected). Although shown as two electrodes located at the distal end 159 of the stimulating assembly 118, more than two electroporation electrodes may be present and used for electroporation.

As noted elsewhere herein, electrodes configured for use in performing electroporation, such as electrodes 150(1) and 150(2), are referred to as "electroporation electrodes." The electroporation electrodes 150(1)/150(2), and the external electroporation device 160, are collectively referred to herein as an "electroporation sub-system" 164. In the embodiments of FIGS. 1A and 1B, the electroporation system 164 is referred to as being integrated with the cochlear implant system 100.

Electroporation electrodes 150(1) and 150(2) are structurally distinguishable from the stimulation electrodes 126 (1)-126(23) in that the electroporation electrodes are not connected to the stimulator unit 120, whereas the stimulation electrodes 126(1)-126(23) must be connected to the stimulator unit 120 to enable operation thereof. In particular, the high voltages associated with electroporation could damage the stimulator unit 120 and, as such, the stimulation electrodes 126(1)-126(23) cannot be used to perform electroporation. In addition, in order to perform electroporation while the stimulation electrodes 126(1)-126(23) are implanted, the electroporation electrodes 150(1) and 150(2) must be electrically isolated from the stimulator unit 120. Presented herein are techniques to electrically isolate the stimulator unit 120 from the electroporation electrodes 150 (1) and 150(2), and thus the high voltage electroporation signals, with an electroporation shield.

Electroporation may have a number of associated purposes. In certain examples, the electroporation is used to open the pores in the cells in the presence of a treatment material (therapeutic agent) in order to enable an effective amount of the therapeutic agent to enter the electroporated (opened) cells. As used herein, the term "therapeutic agent" or "treatment material" may include, but is not limited to, biological or bioactive substances, chemicals, pharmaceutical agents, nanoparticles, ions, including nucleic acids (e.g., Deoxyribonucleic acid (DNA), DNA cassettes, cDNA, or plasmids, Ribonucleic acid (RNA) molecules, RNAi, etc.), proteins, peptides (e.g., Brain-derived neurotrophic factors, etc.), hormones, etc. Therefore, in accordance with certain embodiments, prior to electroporation, a therapeutic agent may first be delivered to the cochlea 137. Such a therapeutic agent may be delivered in a number of different manners, such as through an implantation tool, substance delivery device (e.g., lumen, syringe, etc.), a coating on the stimulating assembly 118, etc.

As noted, the cochlear implant system 100 includes the external coil 106 and the implantable coil 122. The coils 106 and 122 are typically wire antenna coils each comprised of multiple turns of electrically insulated single-strand or multi-strand platinum or gold wire. Generally, a magnet is fixed relative to each of the external coil 106 and the implantable coil 122. The magnets fixed relative to the external coil 106 and the implantable coil 122 facilitate the operational alignment of the external coil with the implantable coil. This operational alignment of the coils 106 and 122 enables the external component 102 to transmit data, as well as possibly power, to the implantable component 104 via a closely-coupled wireless link formed between the external coil 106 with the implantable coil 122. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1B illustrates only one example arrangement.

As noted above, sound processing unit 112 includes the processing module 125. The processing module 125 is configured to convert input audio signals into stimulation control signals 136 for use in stimulating a first ear of a recipient (i.e., the processing module 125 is configured to perform sound processing on input audio signals received at the sound processing unit 112). Stated differently, the sound processor 131 (e.g., one or more processing elements implementing firmware, software, etc.) is configured to convert the captured input audio signals into stimulation control signals 136 that represent stimulation signals for delivery to the recipient. The input audio signals that are processed and converted into stimulation control signals may be audio signals received via the sound input devices 108, signals received via the auxiliary input devices 109, and/or signals received via the wireless transceiver 111.

In the embodiment of FIG. 1B, the stimulation control signals 136 are provided to the RF transceiver 121, which transcutaneously transfers the stimulation control signals 136 (e.g., in an encoded manner) to the implantable component 104 via external coil 106 and implantable coil 122. That is, the stimulation control signals 136 are received at the RF interface circuitry 124 via implantable coil 122 and provided to the stimulator unit 120. The stimulator unit 120 is configured to utilize the stimulation control signals 136 to generate stimulation signals (e.g., current signals) for delivery to the recipient's cochlea via one or more stimulation electrodes 126(1)-126(22). In this way, cochlear implant system 100 electrically stimulates the recipient's auditory nerve cells, bypassing absent or defective hair cells that normally transduce acoustic vibrations into neural activity, in a manner that causes the recipient to perceive one or more components of the input audio signals.

As noted, electroporation refers to the application of an electrical field to a cell such that pores are opened in the cell membrane. When these cells are opened in the presence of a treatment substances, such as neural growth factor genes, the treatment substances may enter the cell through the cell membrane. After the electrical potential is removed, the pores in the cell membrane close such that the treatment substances remains in the cell.

Also as noted, successful electroporation requires a cell to be exposed to a large electrical field utilizing a voltage that is sufficiently high, such as a voltage in the range of approximately 100 Volts (V) to approximately 150 V, which may damage conventional cochlear implants, namely the stimulation electronics. For this reason, conventional techniques generally rely on the use of a dedicated electroporation array that is temporarily inserted into a spatial region within the body of a recipient (e.g., a cochlea) during surgery. This dedicated electroporation array is used to perform the electroporation procedure and then removed from the cochlea, after which a normal intra-cochlear stimulating array is inserted. Insertion of electrode arrays into the delicate cochlea is always a risk to the recipient, and it is therefore desirable to have only one insertion procedure during surgery. As such, presented herein are techniques that enable electroporation of the cochlea nerve cells while the cochlear implant is implanted in the recipient by isolating the stimulation electronics from the high voltages used during the electroporation.

More specifically, in the example of FIGS. 1A and 1B, the electroporation electrodes 150(1) and 150(2) are used to electroporate the recipient's cochlea nerve cells during implantation of the stimulating assembly 118 into the cochlea 137 (i.e., used during application of an electroporation electrical field to the cochlea). As further described herein, the stimulating assembly 118 may also be equipped with an electroporation shield that serves to electrically insulate (e.g., electrically isolate or shield) the intra-cochlear electrodes 126(1)-126(22), and thus the stimulator unit 120, from the electroporation electrical field applied to the cochlea 137 by the electroporation electrodes 150(1) and 150(2) during electroporation process. Merely for ease of illustration, the electroporation shield has been omitted from FIGS. 1A and 1B.

Figure 2:
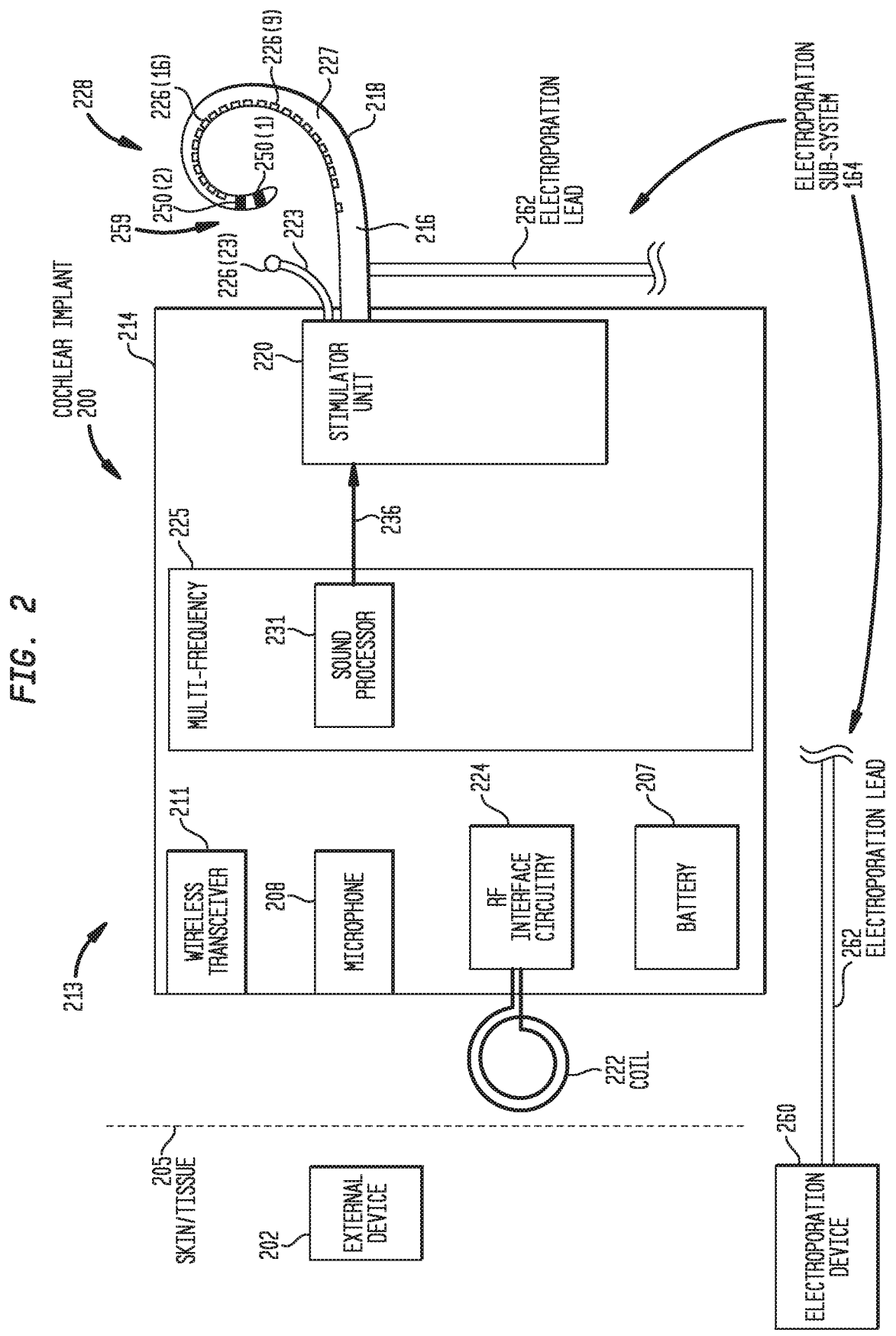
FIG. 2 is a block diagram of a totally implantable cochlear implant, in accordance with certain embodiments presented herein.

FIGS. 1A and 1B illustrate an arrangement in which the cochlear implant 100 includes an external component. However, it is to be appreciated that embodiments of the present invention may be implemented in cochlear implants having alternative arrangements. For example, FIG. 2 is a functional block diagram of an exemplary totally implantable cochlear implant 200 configured to implement embodiments of the present invention. Since the cochlear implant 200 is totally implantable, all components of cochlear implant 200 are configured to be implanted under skin/tissue 205 of a recipient. Because all components are implantable, cochlear implant 200 operates, for at least a finite period of time, without the need of an external device. An external device 202 can be used to, for example, charge an internal power source (battery) 207. External device 202 may be a dedicated charger or a conventional cochlear implant sound processor.

Cochlear implant 200 includes an implant body (main implantable component) 214, one or more input elements 213 for capturing/receiving input audio signals (e.g., one or more implantable microphones 208 and a wireless transceiver 211), an implantable coil 222, and an elongate intra-cochlear stimulating assembly 218.

The stimulating assembly 218 is substantially similar to stimulating assembly 218 described above with reference to FIGS. 1A and 1B. That is, stimulating assembly 218 comprises a carrier member 227 and is configured to be at least partially implanted in the recipient's cochlea. A plurality of longitudinally spaced electrodes 226(1)-226(22) that collectively form a contact or electrode array 228, as well as electroporation electrodes 250(1) and 250(2), are disposed in/on the carrier member 227. Lead region 216 includes a plurality of conductors (wires) that electrically couple the electrodes 226 and to the stimulator unit 220.

Similarly, cochlear implant 200 also comprises an extra-cochlear electrode 226(23), which is substantially similar to extra-cochlear electrode 126(23) described above with reference to FIGS. 1A and 1B. That is, extra-cochlear electrode 226(23) is connected to a lead 223 that includes one or more conductors that electrically couple the extra-cochlear electrode 226(23) to the stimulator unit 220. The intra-cochlear electrodes 226(1)-226(22) and the extra-cochlear electrode 226(23) are sometimes collectively and generally referred to herein as "stimulation electrodes."

FIG. 2 also illustrates that the stimulating assembly 218 includes two (2) electroporation electrode contacts (electrodes) 250(1) and 250(2). As described further below, the electroporation electrodes 250(1) and 250(2) are electrically connected to an external electroporation device 260 via an electroporation lead 262 (e.g., one or more wires). As described elsewhere herein, the electroporation electrodes 250(1) and 250(2) can be used to electroporate the recipient's cochlea nerve cells during implantation of the stimulating assembly 218 into the cochlea. That is, the electroporation electrodes 250(1) and 250(2) may be configured to source, sink, or both source and sink electroporation signals (generated by external electroporation device 260) that result in the application of an electroporation electrical field to the nerve cells of the cochlea. Thereafter, the electroporation electrodes 250(1) and 250(2) can be electrically isolated from the external electroporation device 260 (e.g., electrically disconnected). Although shown as two electrodes located at the distal end 259 of the stimulating assembly 218, the more than two electroporation electrodes may be present and used for electroporation.

As noted elsewhere herein, electrodes configured for use in performing electroporation, such as electrodes 250(1) and 250(2), are referred to as "electroporation electrodes." The electroporation electrodes 250(1)/250(2), and the external electroporation device 260, are collectively referred to herein as an "electroporation sub-system" 264. In the embodiments of FIG. 2, the electroporation sub-system 264 is referred to as being integrated with the cochlear implant 200.

Electroporation electrodes 250(1) and 250(2) are structurally distinguishable from the stimulation electrodes 226(1)-226(23) in that the electroporation electrodes are not connected to the stimulator unit 220, whereas the stimulation electrodes 226(1)-226(23) must be connected to the stimulator unit 220 to enable operation thereof. In particular, the high voltages associated with electroporation could damage the stimulator unit 220 and, as such, the stimulation electrodes 226(1)-226(23) cannot be used to perform electroporation. In addition, in order to perform electroporation while the stimulation electrodes 226(1)-226(23) are implanted, the electroporation electrodes 250(1) and 250(2) must be electrically isolated from the stimulator unit 220. Presented herein are techniques to electrically isolate the stimulator unit 220 from the electroporation electrodes 250(1) and 250(2), and thus the high voltage electroporation signals, with an electroporation shield.

More specifically, in the example of FIG. 2, the electroporation electrodes 250(1) and 250(2) are used to electroporate the recipient's cochlea nerve cells during implantation of the stimulating assembly 218 into the cochlea (i.e., used during application of an electroporation electrical field to the cochlea). As further described herein, the stimulating assembly 218 may also be equipped with an electroporation shield that serves to electrically insulate (e.g., electrically isolate or shield) the intra-cochlear electrodes 226(1)-226(22), and thus the stimulator unit 220, from the electroporation electrical field applied to the cochlea by the electroporation electrodes 250(1) and 250(2) during electroporation process. Merely for ease of illustration, the electroporation shield has been omitted from FIG. 2.

The microphone 208 and/or the implantable coil 222 may be positioned in, or electrically connected to, the implant body 214. The implant body 214 further comprises the battery 207, RF interface circuitry 224, a processing module 225, and a stimulator unit 220 (which is similar to stimulator unit 120 of FIGS. 1A and 1B). The processing module 225 may be similar to processing module 125 of FIGS. 1A and 1B, and includes sound processor 231.

In the embodiment of FIG. 2, the one or more implantable microphones 208 are configured to receive input audio signals. The processing module 225 is configured to convert received signals into stimulation control signals 236 for use in stimulating a first ear of a recipient. Stated differently, sound processor 231 is configured to convert the input audio signals into stimulation control signals 236 that represent electrical stimulation for delivery to the recipient.

As noted above, FIGS. 1A and 1B illustrate an embodiment in which the external component 102 includes the processing module 125. As such, in the illustrative arrangement of FIGS. 1A and 1B, the stimulation control signals 136 are provided to the implanted stimulator unit 120 via the RF link between the external coil 106 and the internal coil 122. However, in the embodiment of FIG. 2 the processing module 225 is implanted in the recipient. As such, in the embodiment of FIG. 2, the stimulation control signals 236 do not traverse the RF link, but instead are provided directly to the stimulator unit 220. The stimulator unit 220 is configured to utilize the stimulation control signals 236 to generate electrical stimulation signals that are delivered to the recipient's cochlea via one or more stimulation channels.

As noted, the techniques presented herein may be implemented in a number of different types of tissue-stimulating prostheses and other implantable medical devices. However, merely for ease of description, further details of the techniques presented herein will generally be described with reference to cochlear implants.

Figures 3A, 3B:
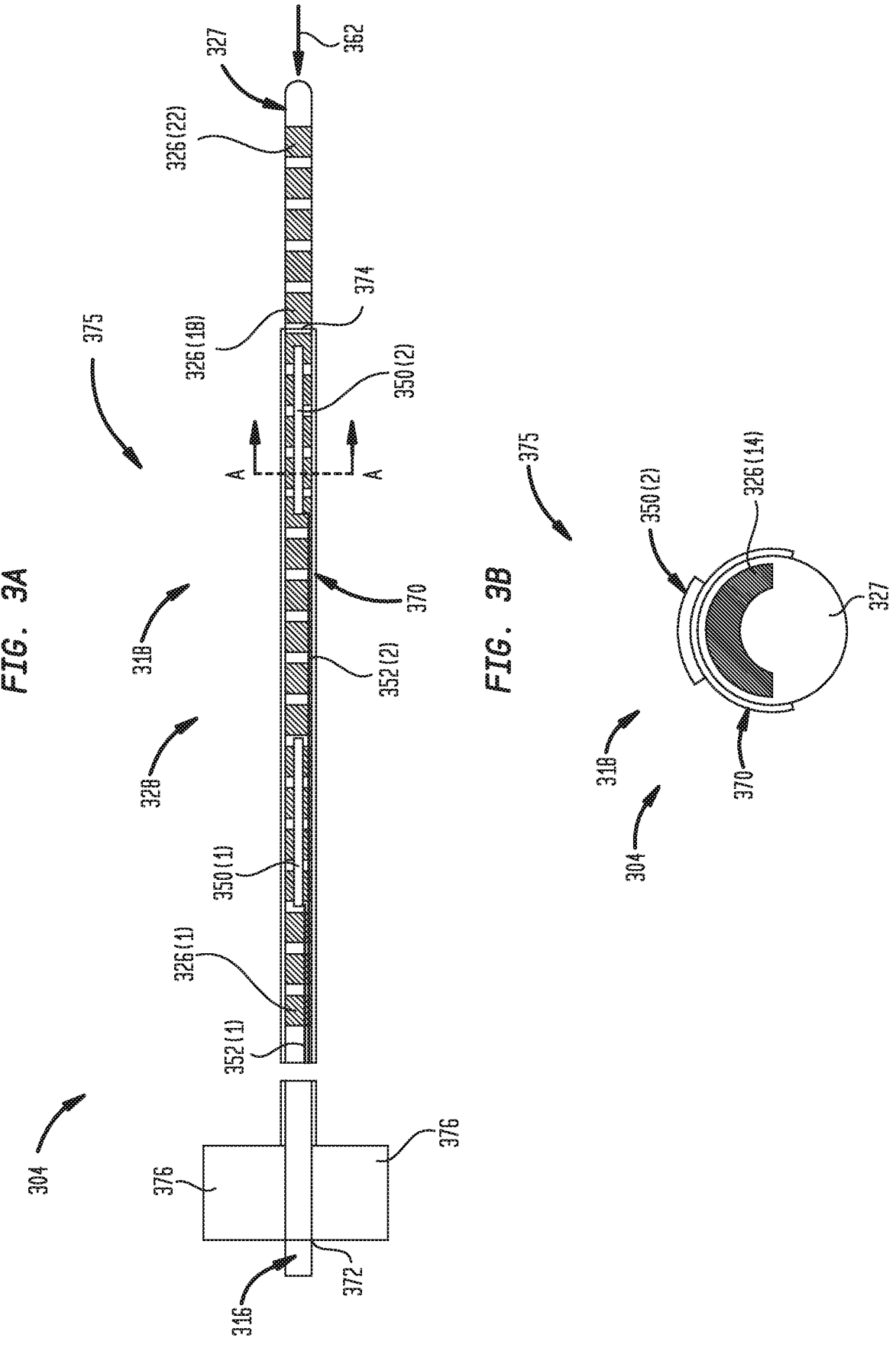
FIG. 3A is a schematic diagram of a stimulating assembly, in accordance with certain embodiments presented herein.
FIG. 3B is a cross-sectional schematic diagram of the stimulating assembly illustrated in FIG. 3A taken along A-A in FIG. 3A, in accordance with certain embodiments presented herein.

FIGS. 3A and 3B illustrate example arrangements in which an "electrical electroporation shield" or "electroporation shield" is disposed around a portion of stimulating assembly of a cochlear implant such that the electroporation shield is at least partially disposed between the electroporation electrodes and the intra-cochlear electrodes of the stimulating assembly. Referring first to FIG. 3A, shown is a simplified schematic side view of a portion of an implantable component 304 (mainly the lead region 316 and intra-cochlear stimulating assembly 318) configured to be implanted in the cochlea of a recipient. FIG. 3A illustrates a specific arrangement in which the stimulating assembly 318 of the implantable component 304 comprises twenty-two (22) intra-cochlear electrodes 326, labeled as electrodes 326(1) through 326(22). The intra-cochlear electrodes 326(1)-326(22) form an electrode array 328. FIG. 3B illustrates a cross-sectional view (taken along section A-A of FIG. 3A) of the stimulating assembly 318 of FIG. 3A where intra-cochlear electrode 326(14) is located. It is to be appreciated that embodiments presented herein may be implemented in alternative arrangements having different numbers of intra-cochlear electrodes.

As shown, intra-cochlear electrode 326(1) is the most basal/proximal intra-cochlear electrode, while intra-cochlear electrode 326(22) is the most distal/apical intra-cochlear electrode. The intra-cochlear electrodes 326(1)-326(22) are each disposed in an electrically-insulating carrier member or body 327 formed, for example, from an elastomer or other resiliently flexible material. The electrodes 326(1)-326(22) are all connected to a stimulator unit via conductors that extend through the carrier member 327 of the stimulating assembly 318 and a lead region 316. For ease of illustration, the conductors and stimulator unit have all been omitted from FIG. 3A.

FIGS. 3A and 3B also illustrates an electroporation shield or insulation sheath 370 that may be disposed over at least a portion of the stimulating assembly 318. The electropo-ration shield 370 may include a first or proximal end 372 and a second or distal end 374. The proximal end 372 of the electroporation shield may be disposed proximate to the lead region 316, while the distal end 374 of the electroporation shield is disposed more proximate to the distal/apical intra-cochlear electrode 326(22) than the proximal end 372. In the illustrated embodiment, the distal end 374 of the electropo-ration shield 370 is disposed between intra-cochlear elec-trode 326(17) and intra-cochlear electrode 326(18). In some embodiments, the distal end 374 of the electroporation shield 370 may be disposed proximate to the distal end (tip) 362 of the carrier member 327, while in other embodiments, the distal end 374 of the electroporation shield 370 may be disposed proximate to any one of the intra-cochlear elec-trodes 326(1)-326(22). As further described below, the length of the electroporation shield 370 (i.e., the distance between the proximal end 372 and the distal end 374 of the electroporation shield 370), and the location of the distal end 374 of the electroporation shield 370, may at least partially correspond to the location of the electroporation electrodes 350(1), 350(2). As best illustrated in FIG. 3A, the proximal end 372 of the electroporation shield 370 may include one or more tabs or protrusions 376. These tabs 376 may be disposed outside of the cochlea when the implantable com-ponent 304 is implanted in a recipient.

Figures 4A, 4B:
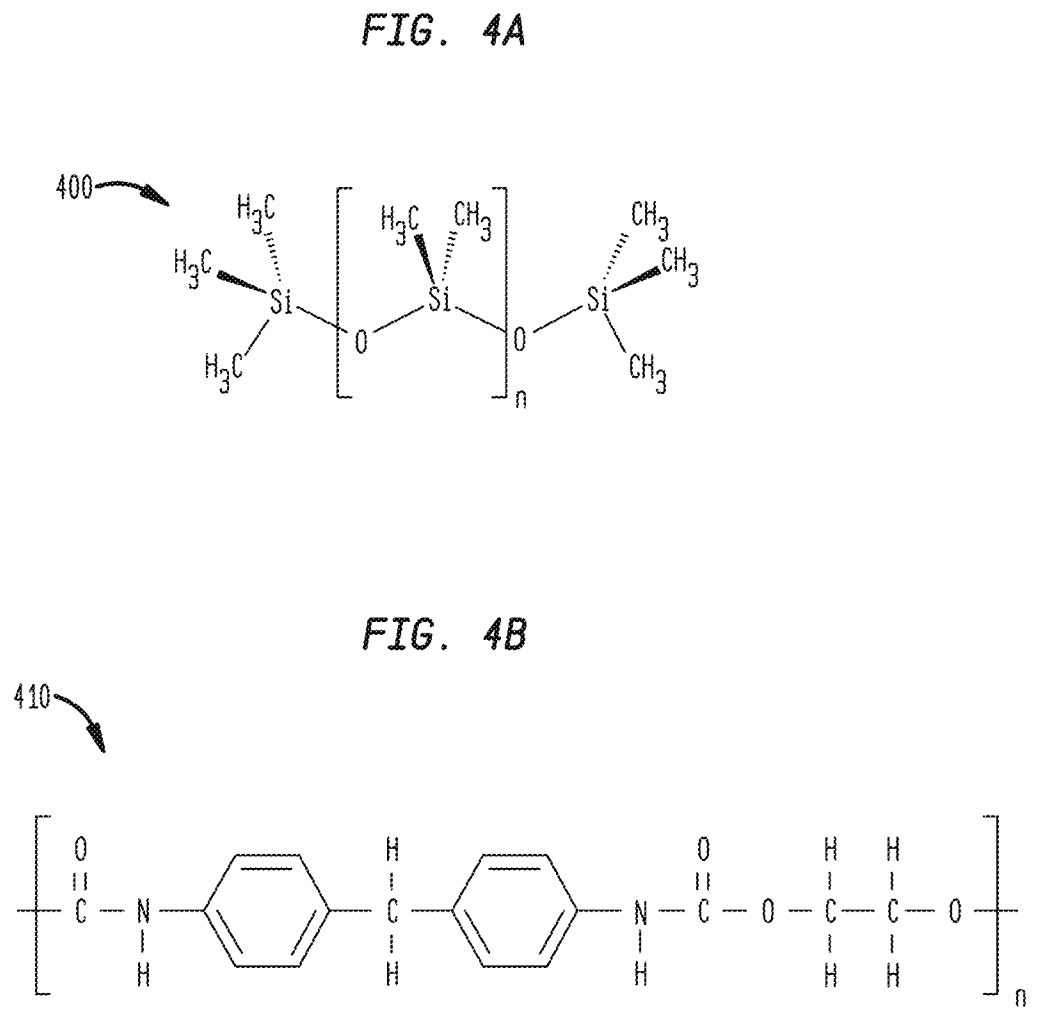

As best illustrated in FIG. 3B, the electroporation shield 370 may not entirely encircle the stimulating assembly 318. Instead, the electroporation shield 370 may encircle only a large enough portion of the stimulating assembly 318 to cover and properly insulate the intra-cochlear electrodes 326, while leaving a portion of the electrically-insulating carrier member or carrier member 327 exposed (i.e., the portion of the carrier member 327 that does not include an intra-cochlear electrode 326). The electroporation shield 370 may be made of a thin and flexible insulating material that insulates the intra-cochlear electrodes 326(1)-326(22) from the electrical field produced by the electroporation elec-trodes 350(1), 350(2) during electroporation. Thus, the elec-troporation shield 370 may be configured to electrically insulate the intra-cochlear electrodes 326(1)-326(2) from voltages generated during electroporation that may reach up to approximately 150 V. The electroporation shield 370 may be constructed from insulating materials such as, but not limited to, polydimethylsiloxane silicone (having the chemi-cal composition 400 illustrated in FIG. 4A), polyurethane (having the chemical composition 410 illustrated in FIG. 4B), etc. Moreover, the electroporation shield 370 must be thin enough to minimize any trauma that may be imparted onto the cochlea and other parts of the recipient during removal of the electroporation shield 370, while being thick enough to pull itself and any attached electroporation elec-trodes 350(1), 350(2) with it. Thus, the electroporation shield 370 may have a thickness in the range of, for example, 5-100 μm.

Returning to FIG. 3A, electroporation electrode 350(1) may be coupled to the outer surface of the electroporation shield 370 and positioned proximate to intra-cochlear elec-trodes 326(4)-326(7), while electroporation electrode 350(2) may also be coupled to the outer surface of the electropo-ration shield 370 but positioned proximate to intra-cochlear electrodes 326(13)-326(17). As best illustrated in FIG. 3B, the electroporation electrode 350(2) is disposed atop the electroporation shield 370 such that the electroporation shield 370 is disposed between the electroporation electrode 350(2) and the intra-cochlear electrodes 326(13)-326(17). While not also illustrated in FIG. 3B, electroporation elec-trode 350(1) is similarly disposed atop the electroporation shield 370 such that the electroporation shield 370 is dis-posed between the electroporation electrode 350(1) and the intra-cochlear electrodes 326(4)-326(7). In some embodi-ments, the electroporation electrodes 350(1), 350(2) may be coupled to the electroporation shield 370 such that the electroporation electrodes 350(1), 350(2) are removed from the stimulating assembly 318 when the electroporation shield 370 is removed from the stimulating assembly 318. In other embodiments, the electroporation electrodes 350(1), 350(2) may be loosely coupled to the electroporation shield 370, or simply placed atop the electroporation shield 370, such that the electroporation electrodes 350(1), 350(2) may be removed prior to removing the electroporation shield 370, or vice versa. The electroporation electrode positions shown in FIG. 3A may be used, for example, to provide electroporation at two locations (e.g., distal and proximal) in the cochlea. The electroporation shield 370 may be posi-tioned on the stimulating assembly 318 as a function of the desired positions of the electroporation electrodes 350(1), 350(2) such that the electroporation shield 370 covers or insulates only the intra-cochlear electrodes 326(1)-326(22) that may be exposed to the high voltage potentials during electroporation (i.e., intra-cochlear electrodes 326(1)-326 (22) positioned far enough away from the electroporation electrodes 350(1), 350(2) may not need to be electrically insulated by the electroporation shield 370).

The electroporation electrodes 350(1), 350(2) are con-nected to an external electroporation system/device (not shown). However, unlike the electrodes 326(1)-326(22), conductors or leads 352(1), 352(2) extend from the elec-troporation electrode 350(1), 352(2), respectively, across the outer surface of the electroporation shield 370 through to the electroporation device. In the embodiment illustrated in FIGS. 3A and 3B, the electroporation electrode conductors 352(1), 352(2) may be thin enough and flexible enough to minimize any trauma that may be imparted onto the cochlea during removal of the electroporation electrodes 350(1), 350(2), but may be thick enough to reduce the impedance of the conductors 352(1), 352(2) below 1 kΩ. Thus, the elec-troporation electrode conductors 352(1), 352(2) may have a depth and/or diameter of, for example, approximately 5-25 μm.

The stimulating assembly 318 and the electroporation shield 370 are sometimes collectively and generally referred to herein as an "electroporation shielded stimulation arrangement" 375. That is, as used herein, the term "elec-troporation shielded stimulation arrangement" refers to a structure comprising an electroporation shield coupled to, positioned over, and/or slid over a component of an implantable medical device (e.g., such as stimulating assembly 318 of the implantable component 304) such that the electroporation shield is disposed over and covers a plurality of stimulation electrodes disposed on the component, and electrically connected to, a stimulator unit of the implantable medical device. In addition, electroporation shielded stimulation arrangement 375 presented herein includes one or more electroporation electrodes (e.g., such as electroporation electrodes 350(1), 350(2)) electrically connected to an electroporation device, but electrically insulated/isolated from the plurality of stimulation electrodes and stimulator unit of the implantable medical device. That is, the electroporation shield is disposed between the electroporation electrodes and the plurality of stimulation electrodes. In certain embodiments, the one or more electroporation electrodes are coupled (e.g., securely, loosely, etc.) to an outer surface of the electroporation shield that is disposed on the component of the implantable medical device.

Turning to FIG. 5, illustrated is a flowchart of a method 500 in accordance with certain embodiments presented herein. For ease of description, method 500 will be described with reference to the arrangement shown in FIGS. 3A and 3B.

The method 500 of FIG. 5 begins at 510 where the electroporation shielded stimulation arrangement 375 is positioned proximate to cells of the recipient. In one example, electroporation shielded stimulation arrangement 375 is positioned proximate to the cells within the cochlea of a recipient. However, as noted elsewhere herein, an electroporation shielded stimulation arrangement 375 may be positioned at other locations, and proximate to other cells, of a recipient.

Returning to the example of FIG. 5, at 520 an electroporation electrical field is applied to the cells of the recipient using at least one of the one or more electroporation electrodes 350(1), 350(2). At 530, the electroporation electrodes 350(1), 350(2) and the electroporation shield 370 are physically removed from the stimulating assembly 318 by sliding, pulling, folding, etc., the electroporation shield 370 to expose the plurality of stimulation electrodes 326(1)-326(22) to the cells of the recipient. In the example embodiment illustrated in FIGS. 3A and 3B, after electroporation, the electroporation shield 370 and the electroporation electrodes 350(1), 350(2) can be removed from the implantable component 304 and electrically isolated from the electroporation device (e.g., electrically disconnected by severing the connection thereto).

In certain, embodiments, a pulling force may be applied to tabs 376 of the electroporation shield 370 to slide or pull the electroporation shield 370 along the carrier member 327 and the lead region 316 until the electroporation shield 370 is no longer present within the cochlea of the recipient. Because the electroporation electrodes 350(1), 350(2) are coupled to the electroporation shield 370, when the electroporation shield 370 slides out of the cochlea via the pulling force applied to the tabs 376, the electroporation electrodes 350(1), 350(2) also slide out of the cochlea. Thus, the electroporation shield 370 provides both electrical insulation to the intra-cochlear electrodes 326(1)-326(22) of the stimulating assembly 318 during electroporation, and facilitates removal of the electroporation electrodes 350(1), 350(2) after electroporation.

Figures 6A, 6B:
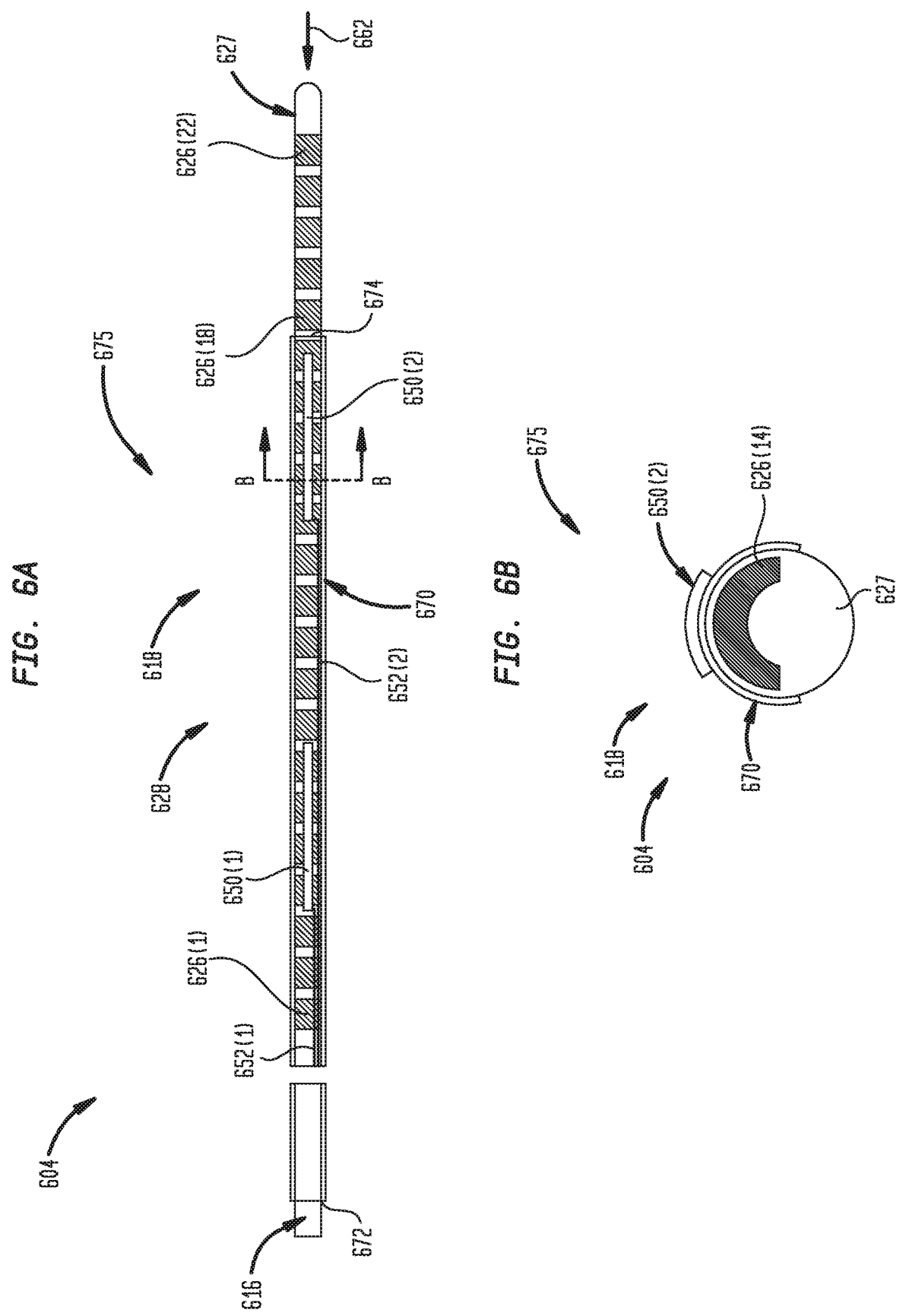
FIG. 6A is a schematic diagram of a stimulating assembly, in accordance with certain embodiments presented herein.
FIG. 6B is a cross-sectional schematic diagram of the stimulating assembly illustrated in FIG. 6A taken along plane B-B in FIG. 6A, in accordance with certain embodiments presented herein.

Referring next to FIGS. 6A and 6B, shown is another embodiment of an electroporation shield disposed around an implantable component of the cochlear implant such that the electroporation shield is at least partially disposed between the electroporation electrodes and the intra-cochlear electrodes of the stimulating assembly. FIG. 6A illustrates a simplified schematic top view of an implantable component 604 (mainly the lead region 616 and intra-cochlear stimulating assembly 618) configured to be implanted in the cochlea of a recipient, while FIG. 6B illustrates a cross-sectional view of the implantable component 604 (taken along section B-B of FIG. 6A). The implantable component 604 of FIGS. 6A and 6B is similar to the implantable component 304 shown in FIGS. 3A and 3B in that the implantable component 604 includes a stimulating assembly 618 that comprises a carrier member 627 and twenty-two (22) intra-cochlear electrodes 626, labeled as electrodes 626(1) through 626(22). Also shown in FIGS. 6A and 6B is an electroporation shield 670 disposed over at least a portion of the intra-cochlear electrodes 626 and electroporation electrodes 650(1), 650(2) disposed on an outer surface of the electroporation shield 670. As shown, the electroporation shield 670 is disposed between the electroporation electrodes 650(1), 650(2) and the intra-cochlear electrodes 626. Conductors 652(1), 652(2) extend from the electroporation electrode 650(1), 652(2), respectively, across the outer surface of the electroporation shield 670 to an electroporation device. The stimulating assembly 618 and the electroporation shield 670 are sometimes collectively and generally referred to herein as an "electroporation shielded stimulation arrangement" 675.

Figures 7A, 7B:
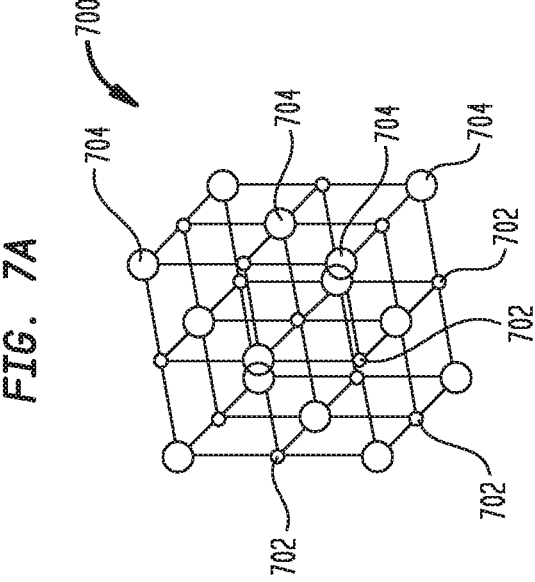
FIG. 7A is a schematic diagram of the chemical structure of a portion of the stimulating assembly illustrated in FIG. 6A, in accordance with certain embodiments presented herein.
FIG. 7B is a schematic diagram of the chemical structure of a portion of the stimulating assembly illustrated in FIG. 7A, in accordance with certain embodiments presented herein.

The electroporation shield 670 illustrated in FIGS. 6A and 6B differs from the electroporation shield 370 of FIGS. 3A and 3B both in the specific structure of the electroporation shield 670, and the material from which the electroporation shield 670 is constructed. More specifically, in the example of FIGS. 6A and 6B, the electroporation shield 670 may not include tabs disposed proximate to the proximal end 672 and the lead region 616. Instead, the electroporation shield 670 is formed from a thin and flexible insulating material that temporarily insulates the intra-cochlear electrodes 626(1)-626(22) from the electrical field produced by the electroporation electrodes 650(1), 650(2) during electroporation, but which dissolves after some period. That is, the electroporation shield 670 is constructed from biocompatible, dissolvable, and electrically insulating material. In certain embodiments, the electroporation shield 670 is formed from a biocompatible, dissolvable, crystalline insulating material such as, but not limited to, sodium chloride (having the chemical composition 700 illustrated in FIG. 7A, and where the sodium molecules are labeled as 702 and the chloride molecules are labeled as 704), sucrose (having the chemical composition 710 illustrated in FIG. 7B), etc. While these crystalline materials act as good electrical insulators in their crystalline phase, the crystalline materials may dissolve when exposed to fluids of the recipient (e.g., the perilymph, etc.) over a predetermined period of time (e.g., over approximately 1 minute, over approximately 5 minutes, over approximately 30 minutes, over approximately 60 minutes, etc.). By forming the electroporation shield 670 from a biocompatible, dissolvable, and electrically insulating material, the electroporation shield 670 may be dissolved within the recipient, which eliminates the need to remove the electroporation shield 670 post electroporation, and only leaves the electroporation electrodes 650(1), 650(2) to be removed, if desired.

In certain embodiments, the electroporation shield 670 can be combined with other reactive agents, including, but not limited to, neurotrophins, anti-inflammatories, etc., so that the reactive agents may be introduced into the recipient when the electroporation shield 670 dissolves. In some embodiments, the electroporation shield 670 may be placed on the stimulating assembly 618 of the implantable component 604 by dip coating the crystalline insulator material of the electroporation shield 670 onto the stimulating assembly 618 such that the electroporation shield 670 covers at least a portion the stimulating assembly 618 that includes the intra-cochlear electrodes 626. The electroporation electrodes 650(1), 650(2) may be coupled to the outer surface of the electroporation shield 670 after the electroporation shield 670 is coupled to the stimulating assembly 618.

Turning to FIG. 8, shown is a flowchart of a method 800 in accordance with certain embodiments presented herein. For ease of description, method 800 will be described with reference to the electroporation shielded stimulation arrangement 675 of FIGS. 6A and 6B.

The method 800 begins at 810 where the electroporation shielded stimulation arrangement is positioned proximate to cells of the recipient. In one specific example, the electroporation shielded stimulation arrangement 675 is positioned proximate to the cells of the cochlea. At 820, an electroporation electrical field is applied to the cells of the recipient using at least one of the one or more electroporation electrodes 650(1), 650(2). At 830, the electroporation shield dissolves within the recipient proximate to the cells of the recipient (in-situ).

In one example, in connection with the electroporation shielded stimulation arrangement 675 of FIGS. 6A and 6B, when the electroporation shield 670 is constructed from biocompatible crystalline materials, exposure of the electroporation shield 670 to fluids within the recipient may cause the electroporation shield 670 to dissolve. The dissolving of the electroporation shield may expose the stimulation electrodes 626(1)-626(22) of the tissue-stimulating prosthesis to the cells of the recipient. In certain embodiments, after the electroporation shield 670 dissolves, the electroporation electrodes 650(1), 650(2) can be removed from the stimulating assembly 618.

In the embodiments of FIGS. 6A-8, the electroporation may occur shortly after insertion of the stimulating assembly 618 into the recipient (i.e., within 1 to 30 minutes of insertion of the stimulating assembly 618) in order to ensure that the electroporation shield 670 has not dissolved prior to electroporation. After the dissolving of the electroporation shield 670, the electroporation electrodes 650(1), 650(2) may be removed from the implantable component 604 and electrically isolated from the electroporation device (e.g., electrically disconnected by severing the connection thereto).

In another example embodiment, the implantable component may only contain a single electroporation electrode disposed proximate to the distal end (tip) of the carrier member. In this example embodiment, the single electroporation electrode may be used in a progressive electroporation process. That is, electroporation signals could be delivered repeatedly, periodically, etc., via the single electroporation electrode as the stimulating assembly is inserted into the cochlea. As a result, electroporation could take place along the entire length of the cochlea (at different points in time during the insertion). Progressive electroporation may also be used with other arrangements.

It is to be appreciated that electroporation electrode positions shown in FIGS. 3A, 3B, 6A, and 6B are illustrative and that electroporation electrodes could be incorporated into a stimulating assembly at other locations. For example, two electroporation electrodes could be placed at the distal end of the stimulating assembly carrier member. In such embodiments, an electroporation shield may be disposed over the distal end of the stimulating assembly carrier member to shield the intra-cochlear electrodes disposed on the distal end of the stimulating assembly carrier member from electroporation signals between the two electroporation electrodes. The positioning and spacing of the electroporation electrodes along the stimulating assembly carrier member may determine which intra-cochlear electrodes are insulated by the electroporation shield. Furthermore, there may not be a need to insulate intra-cochlear electrodes of the stimulating assembly carrier member that are sufficiently spaced from the electroporation electrodes (i.e., those intra-cochlear electrodes may only experience a small and acceptable voltage during electroporation). In addition, any other cochlear implant electrodes (e.g., extra-cochlear electrodes) that may be in contact with the recipient's tissue during electroporation may need also need to be insulated by the electroporation shield during electroporation.

Embodiments presented herein have primarily been described with reference to cochlear implants. However, as noted elsewhere wherein, the techniques presented herein may also or alternatively be used with other types of tissue stimulating prostheses (e.g., auditory brainstem stimulators, implantable pacemakers, spinal cord stimulators, deep brain stimulators, motor cortex stimulators, sacral nerve stimulators, pudendal nerve stimulators, vagus/vagal nerve stimulators, trigeminal nerve stimulators, retinal or other visual prosthesis/stimulators, occipital cortex implants, diaphragm (phrenic) pacers, pain relief stimulators, other neural or neuromuscular stimulators, etc.). FIG. 9 is a simplified schematic diagram illustrating an example spinal cord stimulator 900 in which embodiments presented herein may be implemented.

The spinal cord stimulator 900 comprises a stimulator unit 920 and a stimulating assembly 918. The stimulating assembly 918 may be implanted in a recipient adjacent/proximate to the recipient's spinal cord 937 and comprises four (4) stimulation electrodes 926, referred to as stimulation electrodes 926(1)-926(4). The stimulation electrodes 926(1)-926(4) are disposed in an electrically-insulating carrier member 976 and are electrically connected to the stimulator 920 via conductors (not shown) that extend through the electrically-insulating carrier member 976. The stimulating assembly 918 also comprises an electroporation electrode 950, which is disposed at the distal end 977 of the carrier member 976. Similar to the stimulation electrodes 926(1)-926(4), the electroporation electrode 950 is also electrically connected to the stimulator 920 via at least one conductor (not shown). The stimulator unit 920 may be configured similar to stimulator units 120, 220, etc. described above.

Disposed at least partially around the stimulating assembly 918 may be an electroporation shield 970 such that the electroporation shield 970 covers the stimulation electrodes 926(1)-926(4). The electroporation shield 970 may be configured similar to electroporation shields 370, 670, etc. described above. The electroporation shield 970 may be configured to electrically insulate the stimulation electrodes 926(1)-926(4) from the electric field generated during electroporation by the electroporation electrode 950. The electroporation shield 970 may be configured to be removed from the stimulating assembly 918, facilitate removal of the electroporation electrode 950, and expose stimulation electrodes 926(1)-926(4) to the recipient's spinal cord 937 similar to electroporation shields 370, 670 and electroporation electrodes 350(1), 350(2), 650(1), 650(2) described above. The electroporation shield 970 and stimulating assembly 918 are collectively referred to as electroporation shielded stimulation arrangement 975.

Similar to the embodiments described above, the electroporation electrode 950 is electrically connected to an external electroporation device 960 via a electroporation lead that, for ease of illustration, has been omitted from FIG. 9. During or after implantation of the stimulating assembly 918, the external electroporation device 960 may use the electroporation electrode 950 to apply an electroporation electrical field to nerve cells in or near the spinal cord 937. Use of the electroporation electrode 950 to apply an electroporation electrical field may include, for example, using the electroporation electrode 950 as a delivery path or return path for high-voltage electroporation signals. The electroporation electrical field is applied while the electroporation shield 970 covers and insulates the stimulation electrodes 926(1)-926(4) from the electroporation electrical field. After electroporation, the electroporation shield 970 may be removed by sliding/pulling the electroporation shield 970 along the carrier member 976 of the stimulating assembly 918, or by dissolving the electroporation shield within the recipient, depending on the type of electroporation shield 970 utilized. In the embodiments where the electroporation electrode 950 is coupled to the electroporation shield 970 and the electroporation shield 970 is pulled out of the recipient along the carrier member 976 of the stimulating assembly 918, the electroporation electrode 950 is pulled out of the recipient along with the electroporation shield 970. In the embodiments where the electroporation electrode 950 is coupled to the electroporation shield 970 and the electroporation shield 970 is dissolved within the recipient, the electroporation electrode 950 may be pulled out of the recipient along the carrier member 976 of the stimulating assembly 918.

Following implantation and electroporation, the stimulation electronics 933, generate stimulation signals for delivery to the spinal cord 937 via stimulation electrodes 926(1)-926(4). Although not shown in FIG. 9, an external controller may also be provided to transmit signals through the recipient's skin/tissue to the stimulation electronics 933 for control of the stimulation signals.

FIG. 10 is a flowchart of a method 1000, in accordance with certain embodiments presented herein. Method 1000 begins at 1010 where an electroporation-shielded stimulation arrangement of an implantable medical device is positioned proximate to cells of a recipient of the implantable medical device. At 1020, an electroporation electrical field is applied to the cells of the recipient using one or more electroporation electrodes of the electroporation-shielded stimulation arrangement. At 1030, one or more stimulation electrodes of the electroporation-shielded stimulation arrangement are exposed, in-situ.

FIG. 11 is a flowchart of a method 1100, in accordance with certain embodiments presented herein. Method 1100 begins at 1110 where an electroporation-shielded stimulation arrangement comprising one or more stimulation electrodes disposed in a carrier member and electrically connected to a stimulator unit of an implantable medical device is provided. The one or more electroporation electrodes electrically are connected to an electroporation device, and an electroporation shield covering the one or more stimulation electrodes to electrically isolate the one or more stimulation electrodes from the one or more electroporation electrode. At 1120, the electroporation-shielded stimulation arrangement is positioned proximate to cells of a recipient of the implantable medical device. At 1130, an electroporation electrical field is applied to the cells of the recipient using at least one of the one or more electroporation electrodes. At 1140, the electroporation shield is removed from proximity to the cells of the recipient to expose the one or more stimulation that were covered by the electroporation shield to the cells of the recipient.

It is to be appreciated that the embodiments presented herein are not mutually exclusive and that the various embodiments may be combined with another in any of a number of different manners.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
positioning an electroporation-shielded stimulation arrangement of an implantable medical device at a location proximate to cells of a recipient of the implantable medical device, wherein the electroporation-shielded stimulation arrangement comprises an electroporation shield attached to a carrier member having one or more stimulation electrodes to electrically isolate the one or more stimulation electrodes;
applying an electroporation electrical field to the cells of the recipient at the location using one or more electroporation electrodes of the electroporation-shielded stimulation arrangement; and
exposing, in-situ, the one or more stimulation electrodes of the electroporation-shielded stimulation arrangement to the cells at the location.

2. The method of claim 1, further comprising:
after the one or more stimulation electrodes are exposed, delivering electrical stimulation signals to the cells of the recipient at the location.

3. The method of claim 1, wherein the electroporation shield encircles the carrier member to cover and electrically isolate the one or more stimulation electrodes from the one or more electroporation electrodes.

4. The method of claim 1, wherein exposing, in-situ, the one or more stimulation electrodes of the electroporation-shielded stimulation arrangement comprises:
physically removing the electroporation shield from an outer surface of the carrier member.

5. The method of claim 4, wherein the one or more electroporation electrodes are disposed on an outer surface of the electroporation shield, and wherein physically removing the electroporation shield from the outer surface of the carrier member further comprises:
physically removing the electroporation shield and the one or more electroporation electrodes from the carrier member.

6. The method of claim 4, wherein physically removing the electroporation shield from the outer surface of the carrier member further comprises:
sliding the electroporation shield along a portion of the carrier member.

7. The method of claim 1, wherein the electroporation shield is constructed from a biocompatible crystalline material.

8. The method of claim 7, wherein exposing, in-situ, the one or more stimulation electrodes of the electroporation-shielded stimulation arrangement comprises:
allowing the electroporation shield to dissolve, in-situ.

9. The method of claim 8, wherein the one or more electroporation electrodes are disposed on an outer surface of the electroporation shield, and wherein the method further comprises:

allowing the electroporation shield to dissolve to decouple the one or more electroporation electrodes from the electroporation shield; and sliding the one or more electroporation electrodes along a portion of the carrier member to remove the one or more electroporation electrodes from being in proximity to the cells of the recipient.

10. The method of claim 1, wherein the electroporation shield is configured to electrically insulate the one or more stimulation electrodes from voltages produced by the one or more electroporation electrodes when applying the electroporation electrical field.

11. The method of claim 1, further comprising:

covering the one or more stimulation electrodes with the electroporation shield, wherein the one or more stimulation electrodes are electrically connected to a stimulator unit of the implantable medical device; and coupling the one or more electroporation electrodes to an outer surface of the electroporation shield, wherein the one or more electroporation electrodes are electrically connected to an external electroporation device.

12. An apparatus comprising:

a stimulating assembly of an implantable medical device comprising one or more stimulation electrodes disposed in a carrier member, wherein the stimulating assembly is configured for implantation into a location of a spatial region in a body of a recipient of the implantable medical device;

an electroporation shield comprising an inner surface and an outer surface, wherein the inner surface is attached to the stimulating assembly, such that the inner surface covers the one or more stimulation electrodes, wherein implanting the stimulating assembly at the location implants the electroporation shield at the location, and wherein the electroporation shield is configured to detach from the stimulating assembly to expose the one or more stimulation electrodes of the stimulating assembly at the location; and one or more electroporation electrodes coupled to the outer surface of the electroporation shield.

13. The apparatus of claim 12, wherein the electroporation shield has a thickness of approximately 5 μm to approximately 100 μm.

14. The apparatus of claim 12, wherein the electroporation shield has a proximal end and a distal end, and at least one pull tab disposed proximate to the proximal end.

15. The apparatus of claim 12, wherein the electroporation shield is constructed from a biocompatible crystalline material configured to dissolve within the recipient.

16. The apparatus of claim 12, wherein the electroporation shield is configured to electrically insulate at least one of the one or more stimulation electrodes from voltages produced by the one or more electroporation electrodes during an electroporation process.

17. An apparatus comprising:

a tissue-stimulating prosthesis comprising a stimulating assembly and a plurality of stimulation electrodes disposed on the stimulating assembly, the stimulating assembly being configured to be positioned at a location in a recipient of the tissue-stimulating prosthesis proximate to cells of the recipient; and an electroporation shield disposed over at least one of the plurality of stimulation electrodes of the stimulating assembly, wherein the electroporation shield is configured to electrically insulate at least one of the plurality of stimulation electrodes from voltages equal to and greater than approximately 100 volts, and the electroporation shield is removably coupled to the stimulating assembly such that the electroporation shield is configured to be positioned with the stimulating assembly at the location and decoupled from the stimulating assembly to expose the plurality of stimulation electrodes at the location.

18. The apparatus of claim 17, wherein the electroporation shield has a thickness of approximately 5 μm to approximately 100 μm.

19. The apparatus of claim 17, wherein the electroporation shield has a proximal end and a distal end, and at least one pull tab disposed proximate to the proximal end.

20. The apparatus of claim 19, wherein the at least one pull tab is configured to facilitate removal of the electroporation shield by pulling the electroporation shield along the stimulating assembly of the tissue-stimulating prosthesis and out of proximity to the cells of the recipient.

\* \* \* \* \*